US010806445B2

(12) United States Patent
Penna et al.

(10) Patent No.: US 10,806,445 B2
(45) Date of Patent: Oct. 20, 2020

(54) CHIP ASSEMBLY FOR REUSABLE SURGICAL INSTRUMENTS

(71) Applicant: Covidien LP, Mansfield, MA (US)

(72) Inventors: Christopher Penna, Guilford, CT (US); Jonathan W. Sapienza, Orange, CT (US); Anne Nelson, Guilford, CT (US); Paul D. Richard, Shelton, CT (US)

(73) Assignee: Covidien LP, Mansfield, MA (US)

( * ) Notice: Subject to any disclaimer, the term of this patent is extended or adjusted under 35 U.S.C. 154(b) by 346 days.

(21) Appl. No.: 15/459,317

(22) Filed: Mar. 15, 2017

(65) Prior Publication Data
US 2017/0181745 A1 Jun. 29, 2017

Related U.S. Application Data

(63) Continuation of application No. 13/968,563, filed on Aug. 16, 2013, now Pat. No. 9,636,112.

(51) Int. Cl.
*A61B 17/068* (2006.01)
*A61B 17/115* (2006.01)
(Continued)

(52) U.S. Cl.
CPC ........ *A61B 17/068* (2013.01); *A61B 17/1155* (2013.01); *A61B 90/90* (2016.02);
(Continued)

(58) Field of Classification Search
CPC ... A61B 17/068; A61B 90/98; A61B 17/1155; A61B 2090/0803; A61B 2090/0814;
(Continued)

(56) References Cited

U.S. PATENT DOCUMENTS

| 489,570 A | * | 1/1893 | Scribner | 439/188 |
| 2,768,234 A | * | 10/1956 | Popp | H01R 13/703 381/123 |

(Continued)

FOREIGN PATENT DOCUMENTS

| CN | 101686832 A | 3/2010 |
| EP | 2316345 A1 | 5/2011 |

(Continued)

OTHER PUBLICATIONS

Chip EEPROM PDF (Year: 2012).*
(Continued)

*Primary Examiner* — Robert F Long
(74) *Attorney, Agent, or Firm* — Carter, DeLuca & Farrell LLP

(57) ABSTRACT

A chip assembly for use in a surgical stapler is provided. The chip assembly includes a housing assembly and a plug assembly. The housing assembly includes a base member, seal member, and a circuit board assembly. The base member defines a cavity for receipt of the circuit board assembly and the seal member is configured to be received about an open end of the base member. The plug assembly is configured to selectively engage the open end of the base member. The plug assembly includes a plug member and first and second contact members extending from the plug member. The first and second contact members are configured to be received within the cavity defined by the base member and engage the circuit board assembly when the plug assembly engages the housing assembly.

17 Claims, 12 Drawing Sheets

(51) Int. Cl.

| | | |
|---|---|---|
| *H01R 12/57* | (2011.01) | |
| *H01R 12/72* | (2011.01) | |
| *A61B 90/98* | (2016.01) | |
| *A61B 90/90* | (2016.01) | |
| *H05K 5/06* | (2006.01) | |
| *H05K 7/14* | (2006.01) | |
| *A61B 17/00* | (2006.01) | |
| *H01R 13/52* | (2006.01) | |
| *A61B 90/00* | (2016.01) | |

(52) U.S. Cl.
CPC ............ *A61B 90/98* (2016.02); *H01R 12/57* (2013.01); *H01R 12/721* (2013.01); *H05K 5/069* (2013.01); *H05K 7/1427* (2013.01); *A61B 2017/00017* (2013.01); *A61B 2017/0023* (2013.01); *A61B 2017/0046* (2013.01); *A61B 2017/00398* (2013.01); *A61B 2017/00473* (2013.01); *A61B 2017/00477* (2013.01); *A61B 2017/00734* (2013.01); *A61B 2090/0803* (2016.02); *A61B 2090/0814* (2016.02); *H01R 13/5224* (2013.01)

(58) Field of Classification Search
CPC    A61B 2017/00734; A61B 2017/00477; A61B 2017/00473; A61B 2017/0023; A61B 2017/00017; A61B 2017/00398
USPC ........... 227/175.1–182.1; 173/29, 46, 50, 90, 173/171, 21
See application file for complete search history.

(56) References Cited

U.S. PATENT DOCUMENTS

| | | | | |
|---|---|---|---|---|
| 2,794,081 | A * | 5/1957 | Luhn | H01H 19/585 200/14 |
| 3,059,347 | A * | 10/1962 | Warner | G09B 5/04 434/157 |
| 3,225,155 | A * | 12/1965 | Duncan | H01R 13/703 200/51.09 |
| 3,476,901 | A * | 11/1969 | Werda | H01H 1/5805 200/292 |
| 3,746,106 | A * | 7/1973 | McCullough | E21B 7/04 340/853.5 |
| 3,749,447 | A * | 7/1973 | Renaud | H01H 1/26 200/43.07 |
| 4,229,061 | A * | 10/1980 | Majors | H01R 13/2421 439/217 |
| 4,276,460 | A * | 6/1981 | Haesly | H01H 1/36 200/11 DA |
| 4,375,897 | A * | 3/1983 | Takada | B60R 22/04 280/804 |
| 4,532,930 | A * | 8/1985 | Crosby | A61N 1/36036 607/57 |
| 4,533,202 | A * | 8/1985 | Pohl | H01R 12/721 439/391 |
| 4,632,128 | A * | 12/1986 | Paglione | A61N 5/04 219/746 |
| 4,731,058 | A | 3/1988 | Doan | |
| 4,749,355 | A * | 6/1988 | Hemmer | H01R 24/542 439/63 |
| 4,760,664 | A * | 8/1988 | Amendola | A01K 85/01 43/17.5 |
| 4,778,965 | A * | 10/1988 | Valenzona | H01H 1/5805 200/284 |
| 4,898,360 | A | 2/1990 | VonHayn et al. | |
| 4,924,127 | A * | 5/1990 | Boireau | F16C 23/045 310/89 |
| 4,934,967 | A * | 6/1990 | Marks | H01R 13/111 439/751 |
| 5,010,876 | A * | 4/1991 | Henley | A61B 1/042 206/438 |
| 5,024,807 | A * | 6/1991 | Hatfield | G21C 3/3206 376/352 |
| 5,030,902 | A * | 7/1991 | Mattinger | B26B 19/286 30/DIG. 1 |
| 5,045,820 | A * | 9/1991 | Leicht | H01P 5/107 333/238 |
| 5,093,593 | A * | 3/1992 | Philipp | A61B 17/1622 310/47 |
| 5,103,139 | A * | 4/1992 | Nilssen | H02M 1/425 315/219 |
| 5,161,131 | A * | 11/1992 | Borchardt | G11B 23/049 369/1 |
| 5,254,871 | A * | 10/1993 | Benavides | H01L 23/057 174/376 |
| 5,275,166 | A * | 1/1994 | Vaitekunas | A61B 8/06 600/439 |
| 5,290,179 | A * | 3/1994 | Weingartner | H01R 24/58 439/669 |
| 5,345,487 | A * | 9/1994 | Johansson | G21C 3/332 376/444 |
| 5,382,932 | A * | 1/1995 | Monti | H01P 1/205 333/245 |
| 5,391,166 | A | 2/1995 | Eggers | |
| 5,478,347 | A * | 12/1995 | Aranyi | A61B 17/29 606/167 |
| 5,518,410 | A * | 5/1996 | Masami | H01R 13/2485 324/750.25 |
| 5,712,543 | A * | 1/1998 | Sjostrom | A61B 17/1626 318/67 |
| 5,747,953 | A * | 5/1998 | Philipp | A61B 17/1626 318/114 |
| 5,893,767 | A * | 4/1999 | Broschard, III | H01H 1/18 439/188 |
| 5,910,105 | A * | 6/1999 | Swain | A61B 1/00128 600/104 |
| 5,911,601 | A * | 6/1999 | Weingartner | H01R 24/58 439/669 |
| 5,954,535 | A | 9/1999 | Lawrence | |
| 5,957,850 | A * | 9/1999 | Marian, Jr. | A61B 8/12 29/25.35 |
| 5,971,801 | A | 10/1999 | Kato et al. | |
| 6,012,537 | A * | 1/2000 | Rountree | E21B 4/02 166/242.1 |
| 6,059,719 | A * | 5/2000 | Yamamoto | A61B 1/00059 600/104 |
| 6,100,613 | A * | 8/2000 | Tanaka | H02K 11/046 310/68 D |
| 6,135,804 | A * | 10/2000 | Lux | H01R 4/2433 439/397 |
| 6,156,984 | A * | 12/2000 | Droessler | H01H 35/02 200/334 |
| 6,188,297 | B1 * | 2/2001 | Akiba | H01L 23/552 257/E23.114 |
| 6,325,659 | B1 * | 12/2001 | Heinzen | H01R 4/2429 439/397 |
| 6,334,791 | B1 * | 1/2002 | Yeh | H01R 13/6616 333/185 |
| 6,436,107 | B1 * | 8/2002 | Wang | A61B 1/00149 318/568.11 |
| 6,471,108 | B1 * | 10/2002 | Shi | B25C 5/025 173/20 |
| 6,727,477 | B1 | 4/2004 | Li-Chen | |
| 6,988,897 | B2 | 1/2006 | Belongia et al. | |
| 7,527,518 | B1 * | 5/2009 | Libby | H01R 4/2412 439/395 |
| 7,556,543 | B2 * | 7/2009 | Weber | H01R 4/2454 439/857 |
| 7,618,294 | B1 * | 11/2009 | Lin | H01R 13/701 200/51 R |
| 7,721,931 | B2 | 5/2010 | Shelton, IV et al. | |
| 7,887,530 | B2 | 2/2011 | Zemlok et al. | |
| 8,154,239 | B2 * | 4/2012 | Katsuki | G05B 23/0256 318/565 |
| 8,160,705 | B2 * | 4/2012 | Stevenson | H05K 9/0039 333/182 |

(56) References Cited

U.S. PATENT DOCUMENTS

| | | | | |
|---|---|---|---|---|
| 8,172,591 B2* | 5/2012 | Wertz | ............... | H01R 12/718 |
| | | | | 439/246 |
| 8,394,086 B2* | 3/2013 | Behnke | ............... | A61B 18/18 |
| | | | | 606/32 |
| 8,397,971 B2 | 3/2013 | Yates et al. | | |
| 8,535,088 B2* | 9/2013 | Gao | ............... | H01R 9/03 |
| | | | | 439/490 |
| 8,628,467 B2 | 1/2014 | Whitman et al. | | |
| 8,862,209 B2 | 10/2014 | Whitman et al. | | |
| 8,899,462 B2* | 12/2014 | Kostrzewski | ... | A61B 17/07207 |
| | | | | 227/175.1 |
| 9,023,042 B1* | 5/2015 | Huron | ............... | A61B 18/1402 |
| | | | | 606/49 |
| 9,065,205 B2* | 6/2015 | Gao | ............... | H01R 13/5808 |
| 9,467,766 B2* | 10/2016 | Gao | ............... | H04R 1/1041 |
| 9,636,112 B2 | 5/2017 | Penna et al. | | |
| 10,049,787 B2* | 8/2018 | Costanzo | ............... | H01B 7/282 |
| 2001/0031975 A1 | 10/2001 | Whitman et al. | | |
| 2001/0056282 A1* | 12/2001 | Sonnenschein | ...... | A61B 1/0005 |
| | | | | 606/139 |
| 2002/0134811 A1* | 9/2002 | Napier | ............... | B24B 23/04 |
| | | | | 227/131 |
| 2002/0151767 A1* | 10/2002 | Sonnenschein | ...... | A61B 1/0005 |
| | | | | 600/117 |
| 2002/0160645 A1* | 10/2002 | Nagamine | ......... | H01R 13/6273 |
| | | | | 439/352 |
| 2003/0040222 A1* | 2/2003 | Price | ............... | H01R 27/02 |
| | | | | 439/638 |
| 2004/0077187 A1* | 4/2004 | Belongia | ............ | H01R 13/6205 |
| | | | | 439/39 |
| 2004/0186390 A1* | 9/2004 | Ross | ............... | A61B 5/083 |
| | | | | 600/532 |
| 2005/0012513 A1* | 1/2005 | Cheng | ............... | G01R 1/07342 |
| | | | | 324/755.05 |
| 2005/0088834 A1* | 4/2005 | Milan | ............... | G06F 1/26 |
| | | | | 361/810 |
| 2005/0100867 A1* | 5/2005 | Hilscher | ............. | A46B 5/0095 |
| | | | | 433/216 |
| 2005/0272565 A1 | 12/2005 | Hao | | |
| 2006/0001920 A1* | 1/2006 | Moreno | ............... | H04N 1/00 |
| | | | | 358/498 |
| 2006/0037766 A1* | 2/2006 | Gass | ............... | B23B 31/123 |
| | | | | 173/20 |
| 2007/0023477 A1 | 2/2007 | Whitman et al. | | |
| 2007/0049084 A1* | 3/2007 | Geismayr | .......... | H01R 13/7032 |
| | | | | 439/188 |
| 2007/0065079 A1* | 3/2007 | Mitamura | ........... | G02B 6/4201 |
| | | | | 385/88 |
| 2007/0072442 A1* | 3/2007 | DiFonzo | ............. | H01R 13/641 |
| | | | | 439/39 |
| 2007/0189781 A1* | 8/2007 | Katogi | ............... | G03G 15/0863 |
| | | | | 399/12 |
| 2008/0171475 A1* | 7/2008 | Antsos | ............... | H01R 24/58 |
| | | | | 439/668 |
| 2008/0183190 A1* | 7/2008 | Adcox | ............... | A61B 17/1655 |
| | | | | 606/130 |
| 2008/0185419 A1* | 8/2008 | Smith | ............... | A61B 17/1114 |
| | | | | 227/179.1 |
| 2008/0242510 A1 | 10/2008 | Topel et al. | | |
| 2009/0054208 A1 | 2/2009 | Wu | | |
| 2009/0090763 A1 | 4/2009 | Zemlok et al. | | |
| 2009/0198253 A1* | 8/2009 | Omori | ............... | A61B 18/18 |
| | | | | 606/130 |
| 2009/0210173 A1* | 8/2009 | Arms | ............... | G01L 1/2225 |
| | | | | 702/42 |
| 2009/0306475 A1* | 12/2009 | Yamamoto | .......... | A61B 1/05 |
| | | | | 600/110 |
| 2010/0001035 A1* | 1/2010 | Sandy | ............... | B25C 5/0228 |
| | | | | 227/138 |
| 2010/0090787 A1* | 4/2010 | Kuramoto | .......... | H01Q 1/273 |
| | | | | 333/24 C |
| 2010/0112871 A1* | 5/2010 | Yin | ............... | H01R 13/502 |
| | | | | 439/669 |
| 2010/0154547 A1* | 6/2010 | Fukada | ............... | B06B 1/0292 |
| | | | | 73/632 |
| 2010/0157552 A1* | 6/2010 | Thom | ............... | H03H 1/00 |
| | | | | 361/752 |
| 2010/0232806 A1* | 9/2010 | Kagaya | ............... | H04B 10/2504 |
| | | | | 398/183 |
| 2011/0001685 A1* | 1/2011 | Yukimoto | .......... | H01Q 1/242 |
| | | | | 343/905 |
| 2011/0021078 A1* | 1/2011 | Iida | ............... | H01R 13/2442 |
| | | | | 439/630 |
| 2011/0022032 A1 | 1/2011 | Zemlok et al. | | |
| 2011/0125138 A1 | 5/2011 | Malinouskas et al. | | |
| 2011/0155784 A1 | 6/2011 | Shelton, IV et al. | | |
| 2011/0174099 A1* | 7/2011 | Ross | ............... | A61B 17/072 |
| | | | | 74/89.32 |
| 2011/0257635 A1* | 10/2011 | Whitman | ........... | A61B 10/0233 |
| | | | | 606/1 |
| 2012/0061447 A1 | 3/2012 | Williams et al. | | |
| 2012/0089131 A1* | 4/2012 | Zemlok | ............. | A61B 17/07207 |
| | | | | 606/1 |
| 2012/0116388 A1 | 5/2012 | Houser et al. | | |
| 2012/0168505 A1* | 7/2012 | Sather | ............... | G06Q 20/322 |
| | | | | 235/449 |
| 2012/0203213 A1* | 8/2012 | Kimball | ......... | A61B 17/320068 |
| | | | | 606/1 |
| 2012/0246919 A1* | 10/2012 | Evans | ............... | H01R 43/042 |
| | | | | 29/753 |
| 2013/0020106 A1* | 1/2013 | Kuehne | ............... | B25F 3/00 |
| | | | | 173/214 |
| 2013/0035006 A1* | 2/2013 | Park | ............... | H01R 12/714 |
| | | | | 439/862 |
| 2013/0051413 A1* | 2/2013 | Chen | ............... | H01S 5/02 |
| | | | | 372/36 |
| 2013/0098966 A1 | 4/2013 | Kostrzewski et al. | | |
| 2013/0131650 A1 | 5/2013 | Whitman et al. | | |
| 2013/0324979 A1 | 12/2013 | Nicholas et al. | | |
| 2014/0081631 A1* | 3/2014 | Zhu | ............... | G10L 21/0208 |
| | | | | 704/226 |
| 2014/0226295 A1* | 8/2014 | Nishio | ............... | H01R 13/42 |
| | | | | 361/759 |
| 2014/0263552 A1* | 9/2014 | Hall | ............... | A61B 17/07207 |
| | | | | 227/176.1 |
| 2015/0014393 A1 | 1/2015 | Milliman | | |
| 2015/0048140 A1 | 2/2015 | Penna et al. | | |
| 2015/0053749 A1 | 2/2015 | Shelton, IV et al. | | |
| 2015/0087187 A1* | 3/2015 | Kifedjian | ............. | H01R 13/665 |
| | | | | 439/620.22 |
| 2015/0183256 A1* | 7/2015 | Mauzy | ............... | B42C 19/04 |
| | | | | 412/8 |
| 2015/0216525 A1 | 8/2015 | Collins et al. | | |
| 2016/0249921 A1* | 9/2016 | Cappola | ............. | A61B 17/072 |
| | | | | 227/175.1 |
| 2016/0249928 A1* | 9/2016 | Cappola | ............. | A61B 17/068 |
| | | | | 227/176.1 |
| 2016/0354140 A1* | 12/2016 | Sharma | ............... | A61B 90/39 |
| 2017/0023752 A1* | 1/2017 | Isenhour | ............. | G02B 6/4293 |
| 2018/0067004 A1* | 3/2018 | Sgroi, Jr. | ............. | A61B 17/115 |
| 2018/0360460 A1* | 12/2018 | Mozdzierz | ......... | A61B 17/3476 |
| 2019/0206569 A1* | 7/2019 | Shelton, IV | ......... | A61B 5/0075 |
| 2019/0336101 A1* | 11/2019 | Chiang | ............... | G06F 3/0412 |
| 2019/0350523 A1* | 11/2019 | Bailey | ............... | A61B 5/0002 |

FOREIGN PATENT DOCUMENTS

| | | |
|---|---|---|
| EP | 2606834 A2 | 6/2013 |
| WO | 09/0039510 | 3/2009 |
| WO | 2013051076 A1 | 4/2013 |

OTHER PUBLICATIONS

Chinese Office Action dated Aug. 17, 2018, issued in CN Appln. No. 2014104039655.

European Search Report EP 14 18 1116 dated Feb. 17, 2015.

Maxim Integrated Brochure (Abridged Data Sheet)—DeepCover

(56) References Cited

OTHER PUBLICATIONS

Secure Authenticator with 1-Wire SHA-256 and 512-Bit User EEPROM, pp. 1-4 and p. 42, 2012.
"IC-On-Line" DS28E15-1-Wire SHA-256 Secure Authenticator with 512-Bit User EEPROM, located at: <http://www.ic-on-line.cn/viewsub.--download>.
Chinese Office Action dated Sep. 1, 2017, issued in CN Application No. 2014104039655.
European Search Report dated Jun. 2, 2017, issued in EP Application No. 17154128.

* cited by examiner

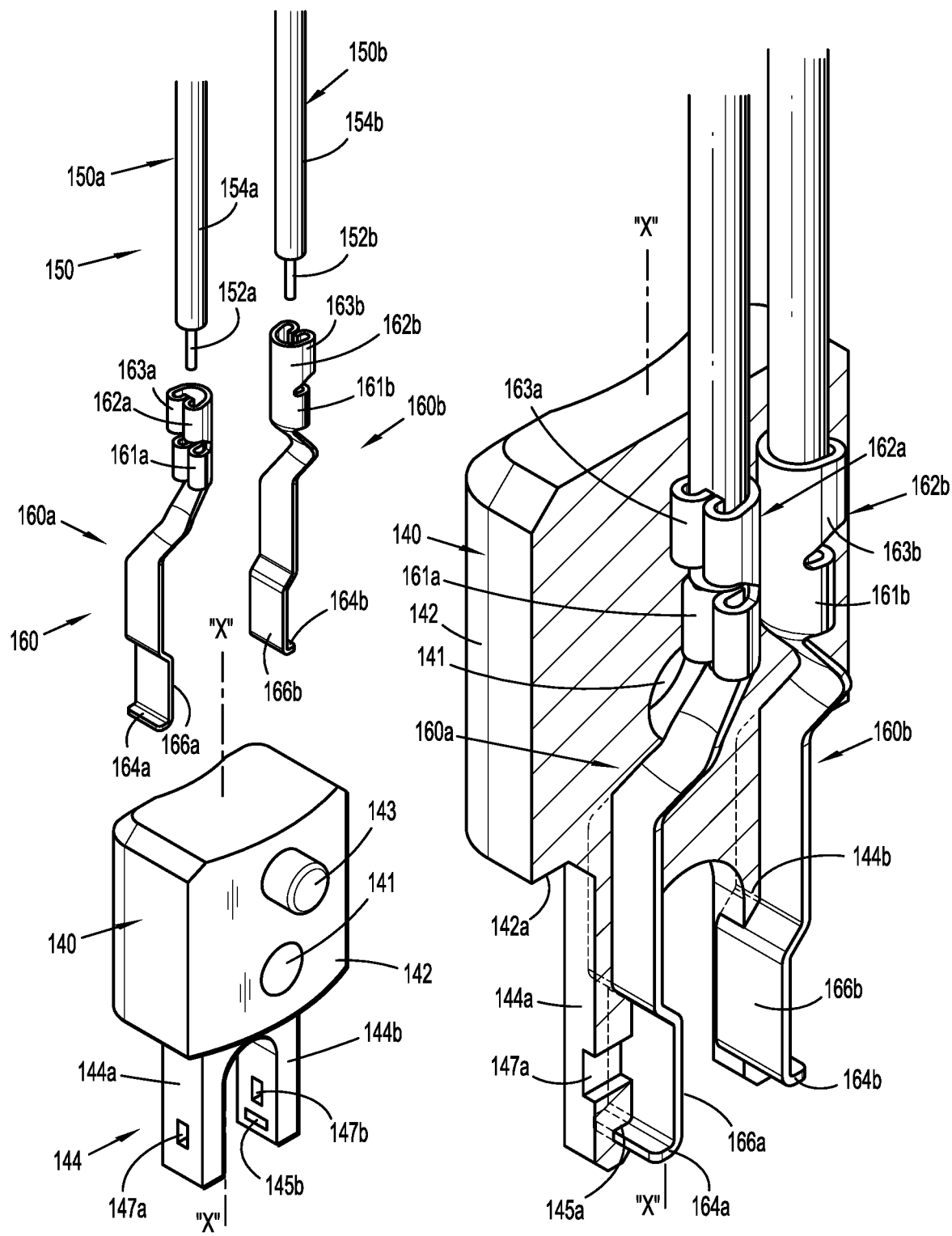

10,806,445 B2

CHIP ASSEMBLY FOR REUSABLE SURGICAL INSTRUMENTS

CROSS-REFERENCE TO RELATED APPLICATIONS

This application is a continuation of U.S. patent application Ser. No. 13/968,563 filed Aug. 16, 2013, and the disclosure of the above-identified application is hereby incorporated by reference in its entirety.

BACKGROUND

Technical Field

The present disclosure relates to surgical instruments having a reusable handle and a disposable end effector. More particularly, the present disclosure relates to a chip assembly for use in a stapling instrument having a disposable loading unit.

Background of Related Art

Powered surgical instruments for use in endoscopic procedures are known. Typically, such instruments include a reusable handle assembly and a disposable end effector. An adapter assembly connects the end effector to the handle assembly. In the case of a surgical stapler, the end effector includes a disposable cartridge or reload assembly that is changed after each firing of the surgical stapler. To reduce costs and shorten procedure times, the handle assemblies are generally configured for use with a variety of reload assemblies of various configurations for use on tissue having different properties, i.e., thickness, density. For example, the different reload assemblies may have staples of different sizes and/or the staples may be arranged in different configurations. To ensure the handle assembly is programmed to operate with the attached reload assembly, some reload assemblies are provided with a chip that communicates to the handle assembly the configuration of the reload assembly. As such, the configuration of the reload assembly is automatically relayed to the handle assembly upon attachment of the reload assembly to the adapter assembly, thereby eliminating any user error that may be experienced during manual programming of the handle assembly when switching between reload assemblies with different configurations.

Surgical staplers are generally used for stapling tissue within a body cavity where the end effector is likely to come in contact with fluids, i.e., blood, bile, irrigation solutions. If any fluids were to contact the chip or the connections between the chip and the handle assembly, the chip would short-circuit, rendering the surgical stapler inoperable.

Therefore, it would be beneficial to have a chip assembly configured to limit exposure of the chip and the connections between the chip and the handle assembly to fluids during a stapling procedure.

SUMMARY

Accordingly, an improved chip assembly for use in a stapling device including a handle assembly, an adapter assembly, and a reload assembly is provided. The chip assembly includes a housing assembly and a plug assembly. The housing assembly including a base member, seal member, and a circuit board assembly. The base member defines a cavity for receipt of the circuit board assembly and the seal member is received about an open end of the base member. The plug is configured to selectively engage the open end of the base member and includes a plug member and first and second contact members extending from the plug member. The first and second contact members are configured to be received within the cavity defined by the base member and engage the circuit board assembly when the plug assembly engages the housing assembly.

In some embodiments, the circuit board assembly includes a chip. The chip may be an EPROM chip. The chip is configured to contain the specifications of a reload assembly in which the housing assembly is mounted. The chip may be writeable. The circuit board assembly may include a pair of contact members. The first and second contact members of the plug member are configured to engage the pair of contact members of the circuit board assembly when the plug assembly engages the housing assembly. The plug member may be monolithically formed. In one embodiment, the plug member is overmolded about the first and second contact members. The plug assembly may further include a pair of arms extending from the plug member. The housing assembly may be configured to be mounted within the reload assembly of the surgical stapler and the plug assembly is configured to be mounted within the adapter assembly. The adapter assembly is configured to interconnect the reload assembly and the handle assembly. The seal member forms a fluid tight seal with base member and the plug member.

Also provided is a surgical stapling device. The stapling device includes a handle assembly, an adapter assembly extending from the handle assembly, a reload assembly operably connected to a distal end of the adapter assembly; and a chip assembly. The chip assembly includes a housing assembly mounted within the reload assembly and a plug assembly mounted within the adapter assembly. The housing assembly may include a base member, seal member, and a circuit board assembly, and the plug assembly may include a plug member and first and second contact members extending from the plug member. The circuit board assembly may be received in a cavity defined by the base member and the seal member may be received about an open end of the base member. The first and second contact members are configured to be received within the cavity defined by the base member. The first and second contact members may engage the circuit board assembly when the reload assembly is operably connected to the adapter assembly.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 10 is an exploded view of the plug assembly shown in FIG. 6;

FIG. 11 is a cross-sectional perspective view of the plug assembly shown in FIG. 6;

DETAILED DESCRIPTION

Figure 1:
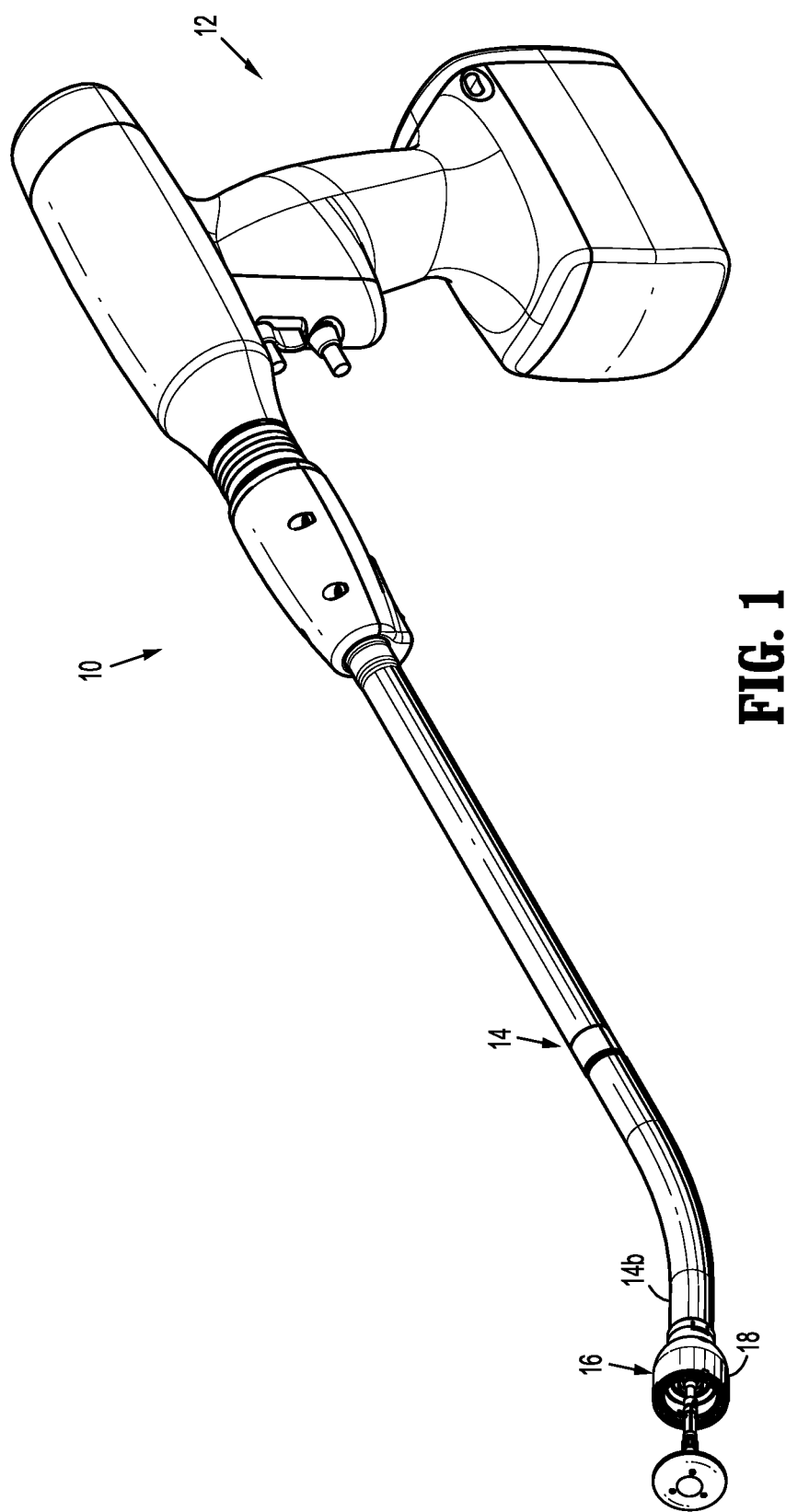
FIG. 1 is a perspective view of a surgical stapling device for use with a chip assembly according to embodiments of the present disclosure.

Embodiments of the presently disclosed chip assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

With reference initially to FIG. 1, a surgical stapling instrument including a chip assembly according to the present disclosure is shown generally as circular stapler 10. Circular stapler 10 includes a handle assembly 12, an adapter assembly 14 removably attached to, and extending distally from handle assembly 12, and a reload assembly 16 selectively secured to a distal end 14b of adapter portion 14. A detailed description of handle assembly 12 and adapter assembly 14 is provided in commonly owned U.S. Patent Appl. Publ. No. 2012/0089131, the content of which is incorporated herein by reference in its entirety. Reload assembly 16 includes a shell member 18 and a pusher member 20 slidably disposed within shell member 18. A proximal end of shell member 18 is selectively secured to distal end 14b of adapter assembly 14 by a slot and tab configuration. A proximal end of pusher member 20 is selectively secured to a distal end of a driver member (not shown) in a similar fashion. In one embodiment, reload assembly 16 is selectively secured to distal end 14b of adapter assembly 14 in the manner described in Chinese Patent Application No. 201310084378.X (203-9030), the content of which is incorporated herein by reference in its entirety.

In any of the embodiments disclosed herein, the reload assembly can be a removable and replaceable component. Further, the stapler may have an elongate shaft that is connected to the handle assembly, rather than a removable and replaceable adapter assembly. In any of the embodiments disclosed herein, the chip assembly can be used in conjunction with other types of reloads, such as electrosurgical reloads, linear endoscopic staplers, transverse staplers, clip appliers, open staplers, etc. Adapter assemblies provide the right number of shafts and type of gearing for interaction with the particular reload. It is contemplated that a system of adapter assemblies and reload assemblies are developed for use with manual and/or powered handle assemblies.

The reload assembly includes an anvil assembly and a cartridge assembly, with a series of surgical staples being disposed in the cartridge assembly. The reload assembly further includes a rod for attachment to the anvil assembly, so that the anvil assembly is movable toward and away from the cartridge assembly with movement of the rod. Tissue is disposed between the anvil assembly and cartridge assembly and then the anvil assembly is approximated with the cartridge assembly to capture the tissue therebetween. The pusher member 20 of the reload assembly 16 drives the staples from the cartridge assembly and then drives a circular knife through the tissue to complete an anastomosis. Separate pusher members can be provided for the staples and knife, or the pusher member 20 can be selectively attached to the knife subsequent to the firing of the staple through the use of a snap ring, latch, or other structure. For example, the pusher arrangement disclosed in U.S. application Ser. No. 13/739,246, filed Jan. 11, 2013, the entire disclosure of which is hereby incorporated by reference herein, can be used.

It is desirable for the lumen of the reload assembly 16 to be relatively large, so that the inner lumen of the resulting anastomosis is relatively large and complications would tend to be reduced. For example, the structure of the outer shell of the cartridge assembly can include ribs or thinned wall portions as disclosed in U.S. application Ser. No. 13/397,039, filed Feb. 15, 2012, the entire disclosure of which is hereby incorporated by reference herein.

After the tissue is cut by the knife, the anvil assembly is moved away from the cartridge assembly and the anvil assembly is removed from the tissue. To facilitate such removal, the anvil assembly can have a tilting mechanism that tilts the anvil, making it easier to remove from tubular tissue portions. In any of the embodiments disclosed herein, the reload assembly can have a tilting mechanism such as, for example, the tilting mechanism disclosed in U.S. publication no. 2012/0211544 A1, the entire disclosure of which is hereby incorporated by reference herein.

In any of the embodiments disclosed herein, the cartridge assembly can have a removable and replaceable staple cartridge, whether or not the reload assembly is also removable and replaceable. The staples are arranged in circular or annular rows and can include staples of different sizes. For example, in any of the embodiments disclosed herein, the staples include an inner row of staples and an outer row of staples, with the staples of the inner row having a smaller size than the staples of the outer row. The cartridge can include a stepped tissue contacting face so that when approximated with the anvil assembly, the gap therebetween is smaller at the inner row of staples than at the outer row of staples.

The handle assembly shown in FIG. 1 desirably has a power source and at least one motor, such as, for example, the handle assembly disclosed in U.S. application Ser. No. 13/444,228, filed Apr. 11, 2012, the entire disclosure of which is hereby incorporated by reference herein. The handle assembly has at least one motor for rotating one or more shafts to drive various components of the reload assembly. For example, the handle assembly can have two rotatable drive shafts and a rechargeable battery. Alternatively, the power source can be a separate generator or connection to another power source. The drive shafts are connected to the adapter assembly or other shaft and rotation is mechanically converted to forward and backward translation of the rod and pusher member discussed above. The mechanical conversion can occur in the adapter assembly or reload assembly.

The handle assembly desirably has a controller for controlling operation of the apparatus, and generating and recording data. In any of the embodiments disclosed herein, the reload assembly can have a chip assembly mounted therein. The chip assembly stores data and interacts with the controller in the handle assembly, or some other computer device for storing and generating data as described herein. The chip assembly can interact and communicate wirelessly or through appropriate wiring.

Figure 2:
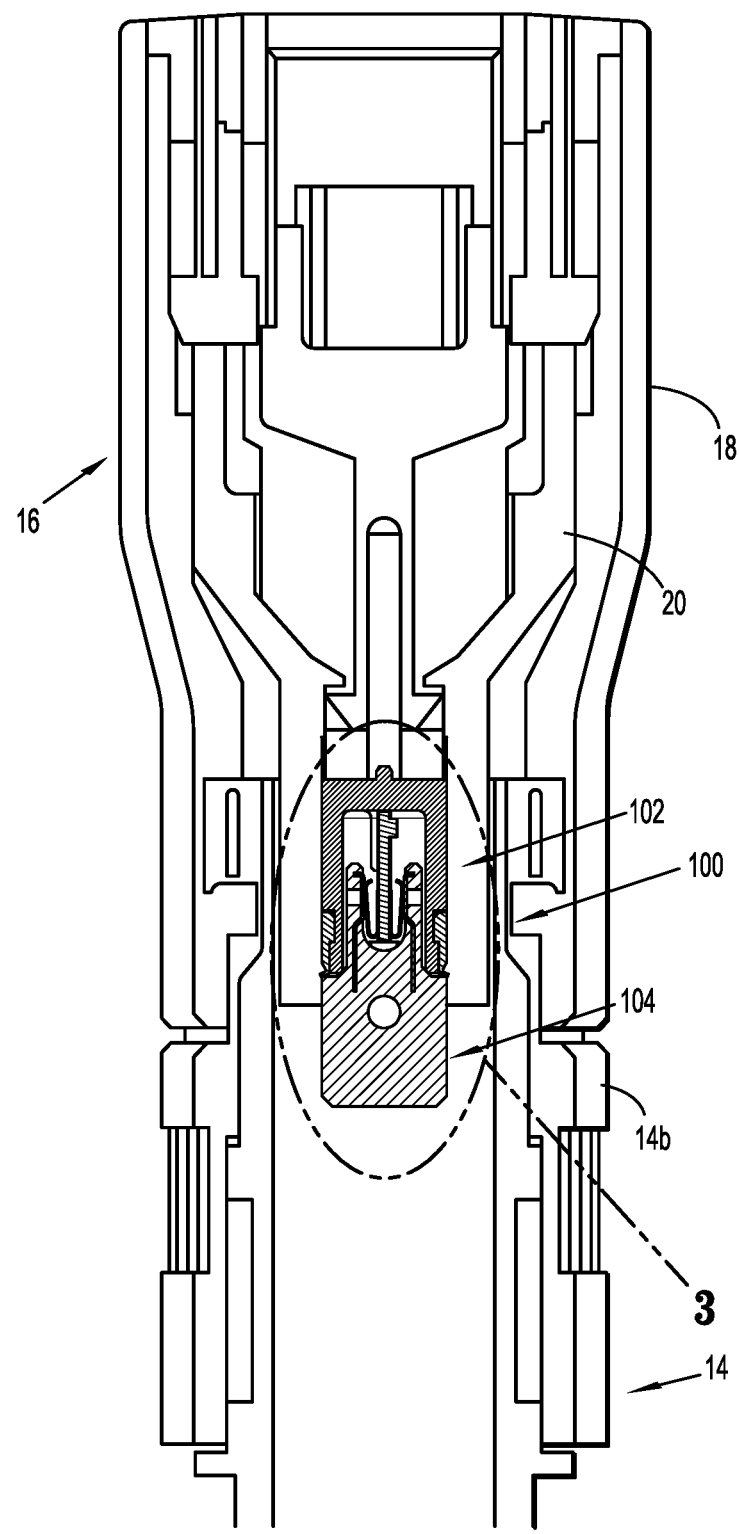
FIG. 2 is a cross-sectional view of the distal end of an adapter assembly and a reload assembly of the surgical stapling device shown in FIG. 1.

With reference now to FIGS. 2-11, chip assembly 100 includes a housing assembly 102 and a plug assembly 104. As seen in FIG. 2, housing assembly 102 is configured to be securely mounted within reload assembly 16, and plug assembly 104 is configured to be securely mounted within distal end 14b of adapter assembly 14. Housing assembly 102 and plug assembly 104 are positioned within respective reload assembly 16 and adapter assembly 14 such that when reload assembly 16 is secured to adapter assembly 14 housing assembly 102 engages plug assembly 104. It is envisioned that one or both of housing assembly 102 and plug assembly 104 may be spring biased towards the other to overcome any manufacturing tolerances between reload assembly 16 and adapter assembly 14.

With particular reference to FIGS. 5-8, housing assembly 102 includes a base member or housing 110, a seal member 120, and a circuit board assembly 130. Base member 110 defines a cavity 111 and includes an open first end 110a and a closed second end 110b. In one embodiment, base member 110 is monolithically formed to ensure cavity 111 is fluid tight. Alternatively, base member 110 may be formed as two components that are joined together in a fluid tight manner, i.e., welding, adhesive.

Still referring to FIGS. 5-8, first end 110a of base member 110 forms an extension 112 configured to engage seal member 120. Specifically, extension 112 is formed by a laterally recessed portion of base member 110. A flange 114 extends about an end of extension 112 and is configured to engage a lip 122 on seal member 120. The reduced outer dimension of extension 112 allows seal member 120 to lay flush with base member 110. As can be appreciated with reference to FIG. 5, the flush configuration of seal member 120 relative to base member 110 reduces the likelihood of seal member 120 from being separated from base member 110 during use. Base member 110 further defines a slot 111a (see FIG. 7) in communication with cavity 111. Slot 111a is configured to selectively receive circuit board assembly 130. Extension 112 defines first and second notches 113a, 113b in alignment with slot 111a. First notch 113a is configured to receive a first inwardly extending tab 124a formed on seal member 120. Second notch 113b is configured to receive a second inwardly extending tab 124b formed on seal member 120. As will be discussed in further detail below, either or both of tabs 124a, 124b may be configured to retain circuit board assembly 130 within slot 111a of base member 110.

With reference still to FIGS. 5-8, base member 110 includes a support member 116 (see FIG. 3) extending from closed second end 110b into cavity 111. Support member 116 is configured to support circuit board assembly 130 when circuit board assembly 130 is received within slot 111a of base member 110. Base member 110 further includes a connection member 118 for securing housing assembly 102 within reload assembly 16 (FIG. 2). As shown, connection member 118 includes an annular flange 118a extending perpendicular to a longitudinal axis "x" of base member 110. Annular flange 118a is configured to be received about a tubular sleeve 22 (FIG. 4) of reload assembly 16. Although shown as annular flange 118a, it is envisioned that connection member 118 may include a C-shaped flanged (not shown) for selective attachment to reload assembly 16. Alternatively, connection member 118 may include one or more tabs and/or one or more slots for connection of reload assembly 16 to base member 110 through a tab and slot configuration. Base member 110 further includes one or more alignment features 119. As shown, alignment feature 119 forms a protrusion extending outwardly from closed second end 110b of base member 110. Alignment feature 119 facilitates alignment of base member 110 within reload assembly 16 and/or prevents rotational movement of housing assembly 102 during transport, loading, and use of reload assembly 16.

With continued reference to FIGS. 5-8, seal member 120 includes a substantially annular body having open first and second ends 120a, 120b. First end 120a includes lip 122 extending about an inner surface of seal member 120. As discussed above, lip 122 is configured to engage flange 114 formed on extension 112 of base member 110. In this manner, seal member 120 forms a fluid tight seal about extension 112 of base member 110. Optionally, seal member 120 is adhered or otherwise bonded to extension 112 to increase the integrity of the seal between seal member 120 and base member 110. Second end 120b of seal member 120 includes first and second inwardly extending tabs 124a, 124b. As discussed above, first tab 124a is configured to be received within first notch 113a defined by extension 112 of base member 110 and second tab 124b (FIGS. 6 and 9) is configured to be received within second notch 113b defined by extension 112 of base member 110 when seal member 120 is secured to base member 110. At least first tab 124a is configured to ensure circuit board assembly 130 is maintained within slot 111a formed in base member 110. A flap 126 extends from second end 120b of seal member 120 and is configured to form a seal between housing assembly 102 and plug assembly 104 when plug assembly 104 engages housing assembly 102.

Figure 8:
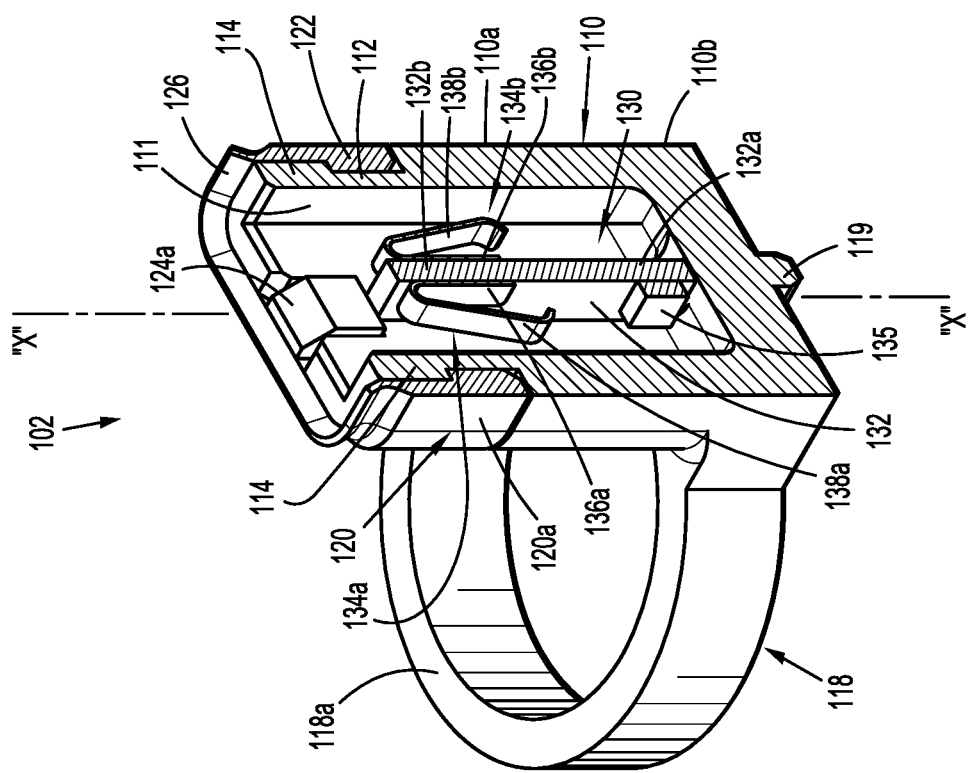
FIG. 8 is a cross-sectional perspective view of the housing assembly shown in FIG. 6.
Figure 7:
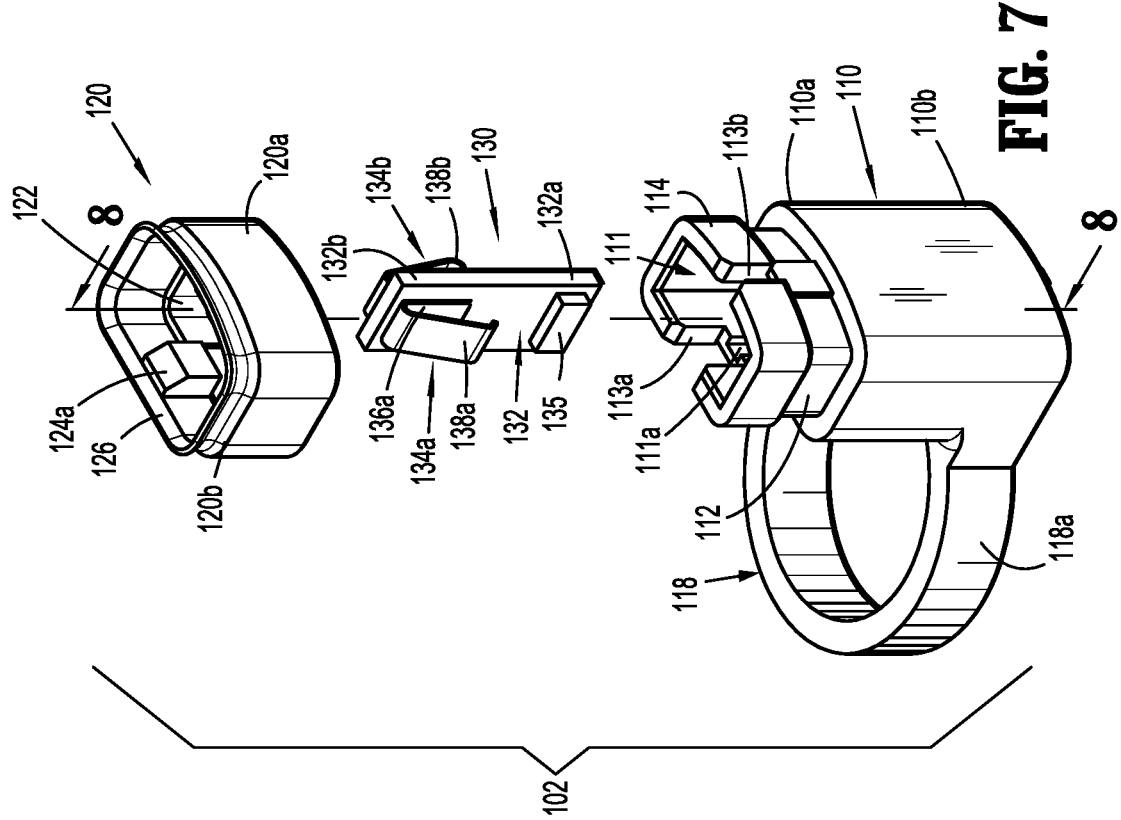
FIG. 7 is an exploded perspective view of the housing assembly shown in FIG. 6.
Figure 9:
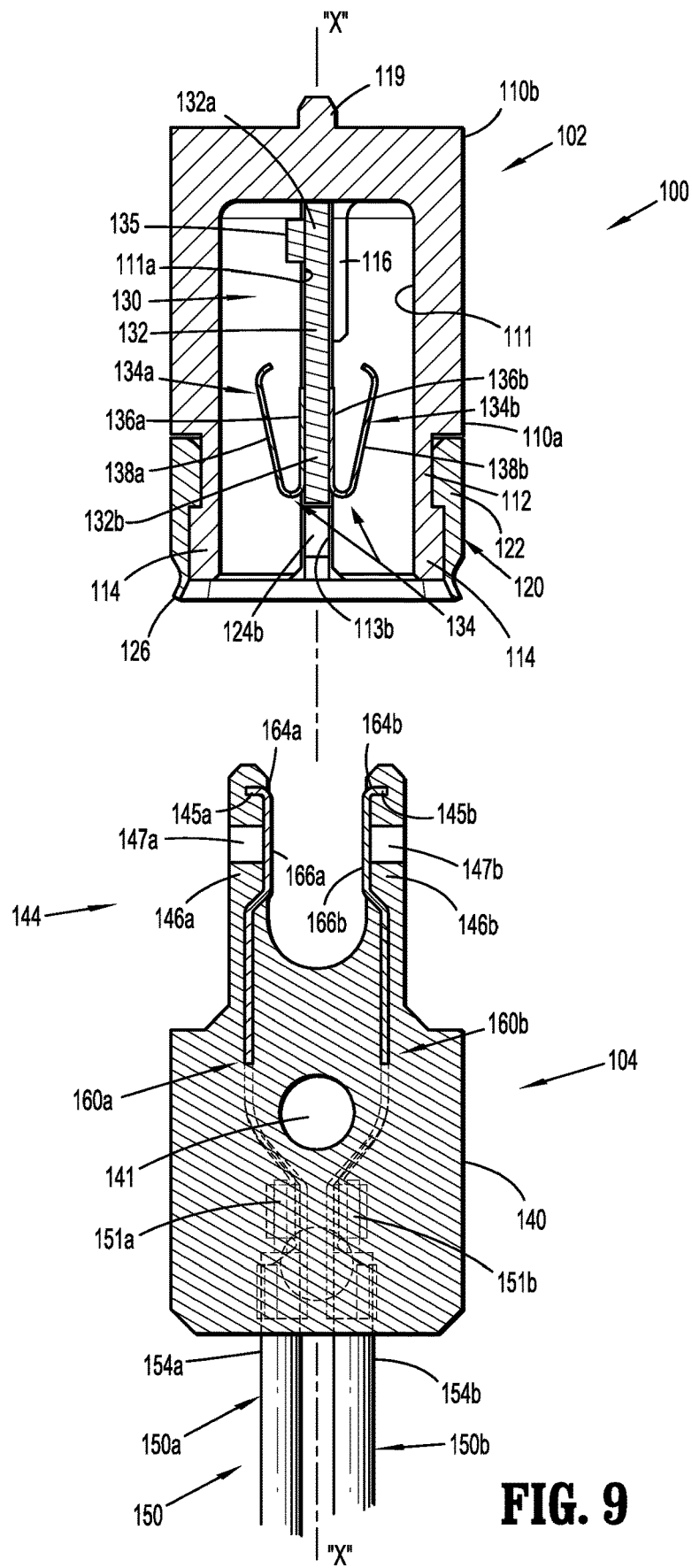
FIG. 9 is a cross-sectional side view of the housing assembly and plug assembly shown in FIG. 6.
Figure 12:
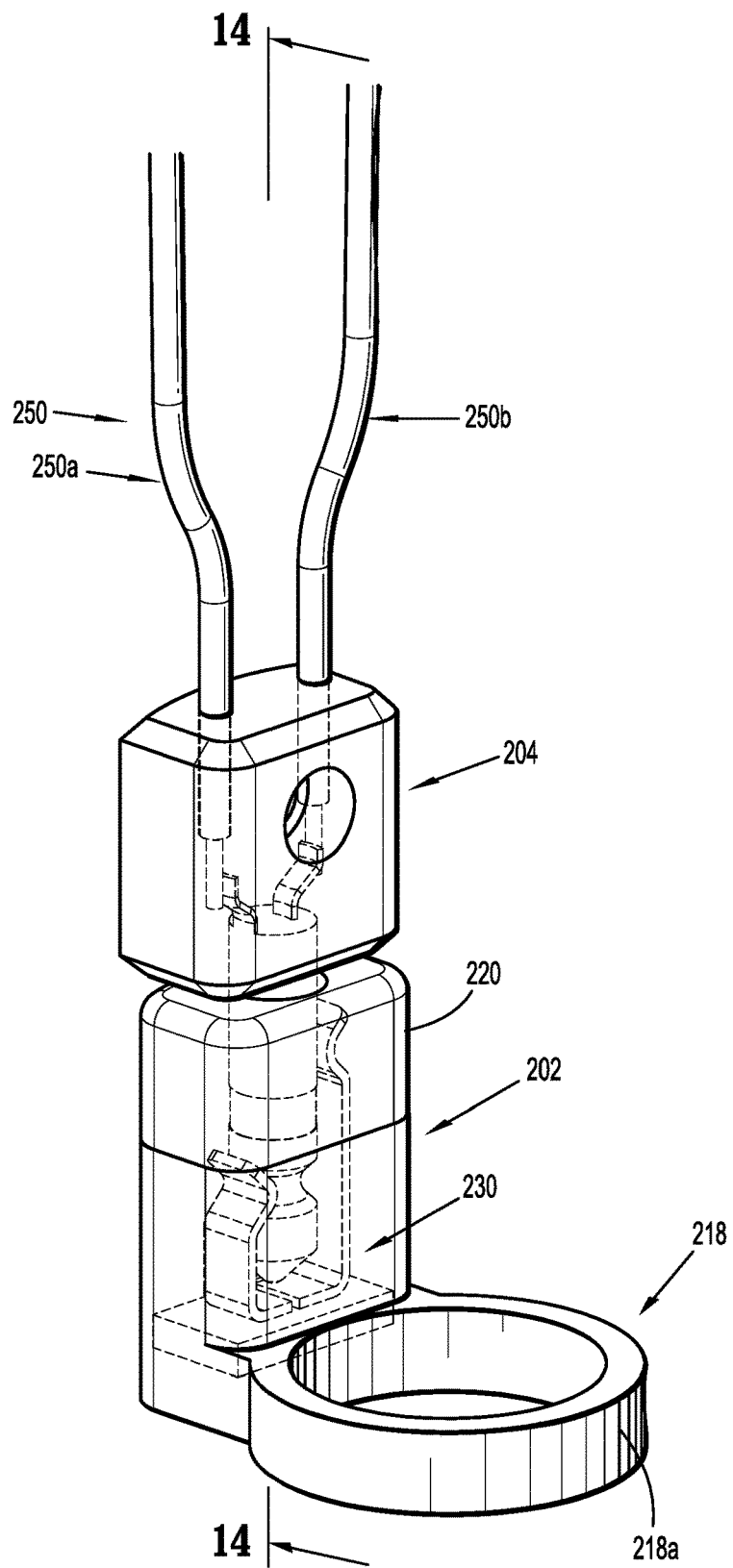
FIG. 12 is a perspective view of a chip assembly according to another embodiment of the present disclosure.

With particular reference now to FIGS. 7-9, circuit board assembly 130 includes a circuit board 132, a pair of contact members 134a, 134b (collectively, contact members 134) and a chip 135. Circuit board 132 defines a substantially planar elongate member configured to be securely received within slot 111a defined by base member 110. Chip 135 is in electrical communication with contact member 134. A first end 132a of circuit board 132 supports chip 135, and a second end 132b of circuit board 132 supports first and second contact members 134a, 134b. Chip 135 includes any commercially available chip capable of storing the specifications of reload assembly 16, i.e., cartridge size, staple arrangement, staple length, clamp-up distance, and transmitting the specifications to handle assembly 12. In one embodiment, chip 135 includes an erasable programmable read only memory ("EPROM") chip. In this manner, the firing forces and/or firing stroke of handle assembly 12 may be adjusted to accommodate the attached reload assembly 16. It is further envisioned that chip 135 may include write capabilities which allow handle assembly 12 to encode that a reload assembly has been used to chip 135 to prevent reuse of an empty reload assembly, or for any other purpose.

In any of the embodiments disclosed herein, the chip 135 stores data representing information such as the type of reload assembly, the size of the staples, the configuration of the reload assembly, the firing forces, the firing stroke, the serial number for the particular reload assembly, the status of the operation (such as whether the reload assembly has been fired), and other information. Through communication with the handle assembly controller or other computer device, reuse of a previously used reload assembly can be prevented. Through communication with the handle assembly controller or other computer device, the operation of the reload assembly can be controlled to have the appropriate firing forces, firing stroke, etc. Through communication with the handle assembly controller or other computer device, unauthorized reloads can be disabled, and the handle assembly can be controlled to avoid using such unauthorized reloads.

Figure 3:
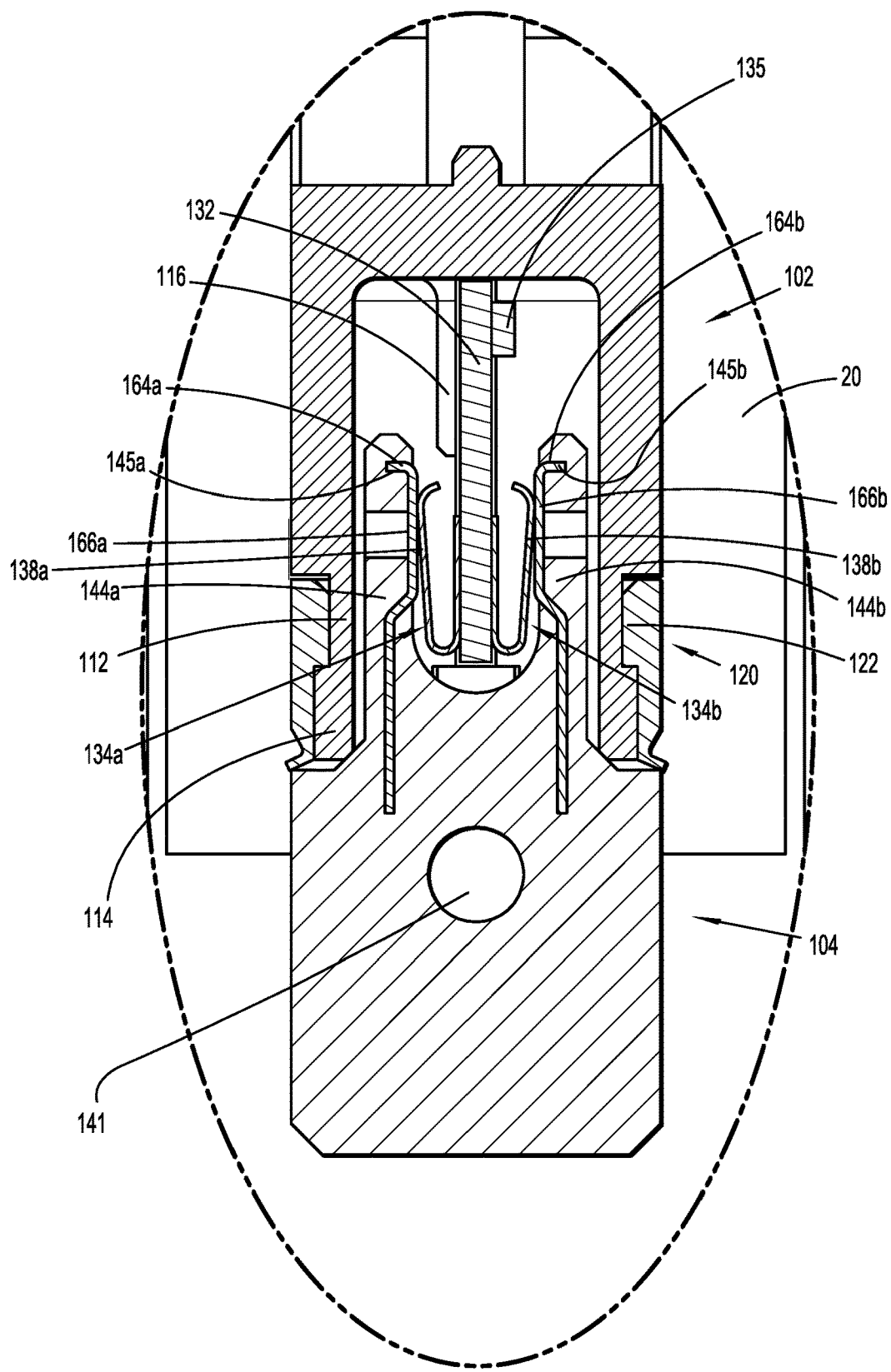
FIG. 3 is an enlarged view of the indicated area shown in FIG. 2.
Figure 4:
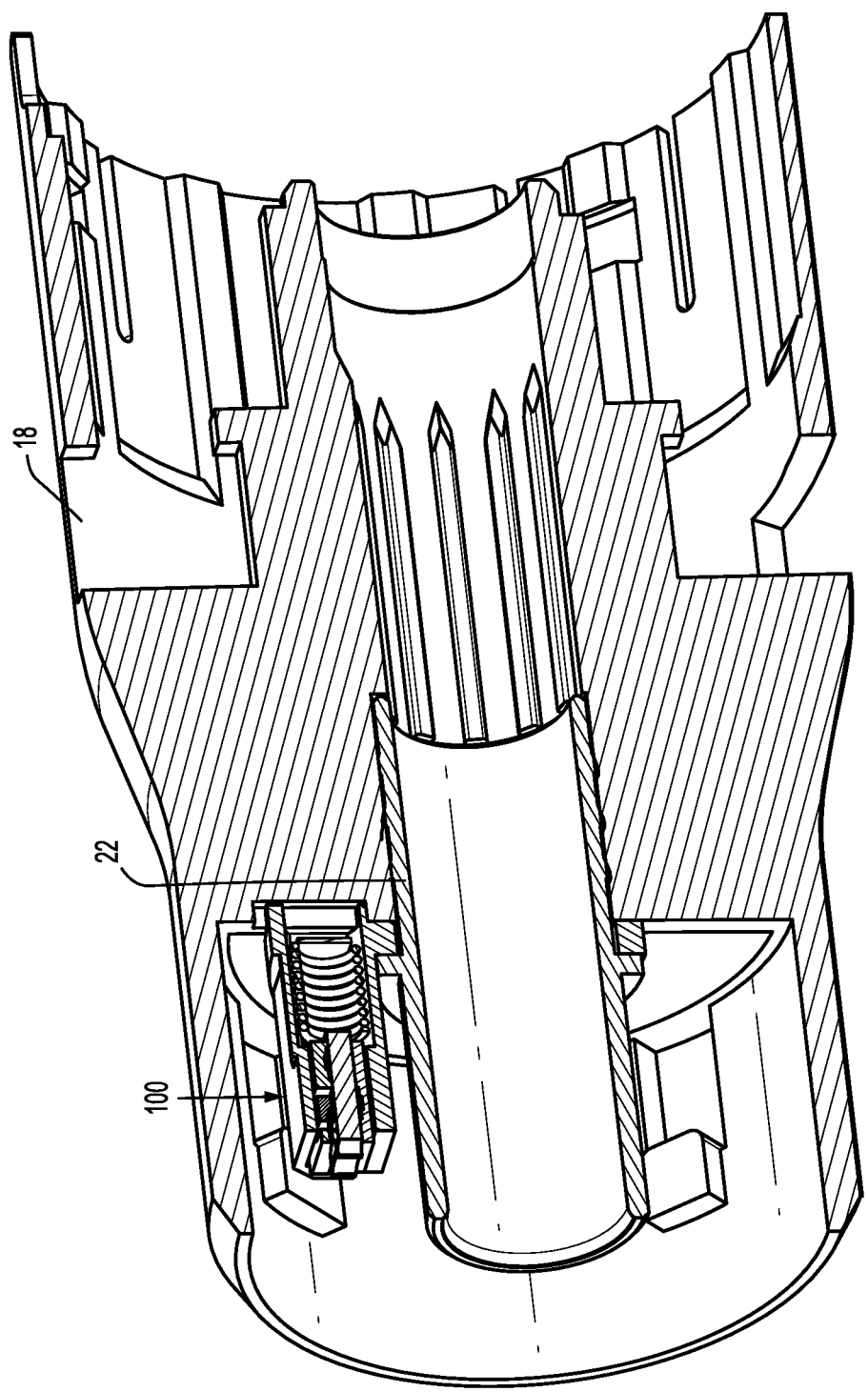
FIG. 4 is another cross-sectional view of the reload assembly shown in FIG. 1.
Figures 5, 6:
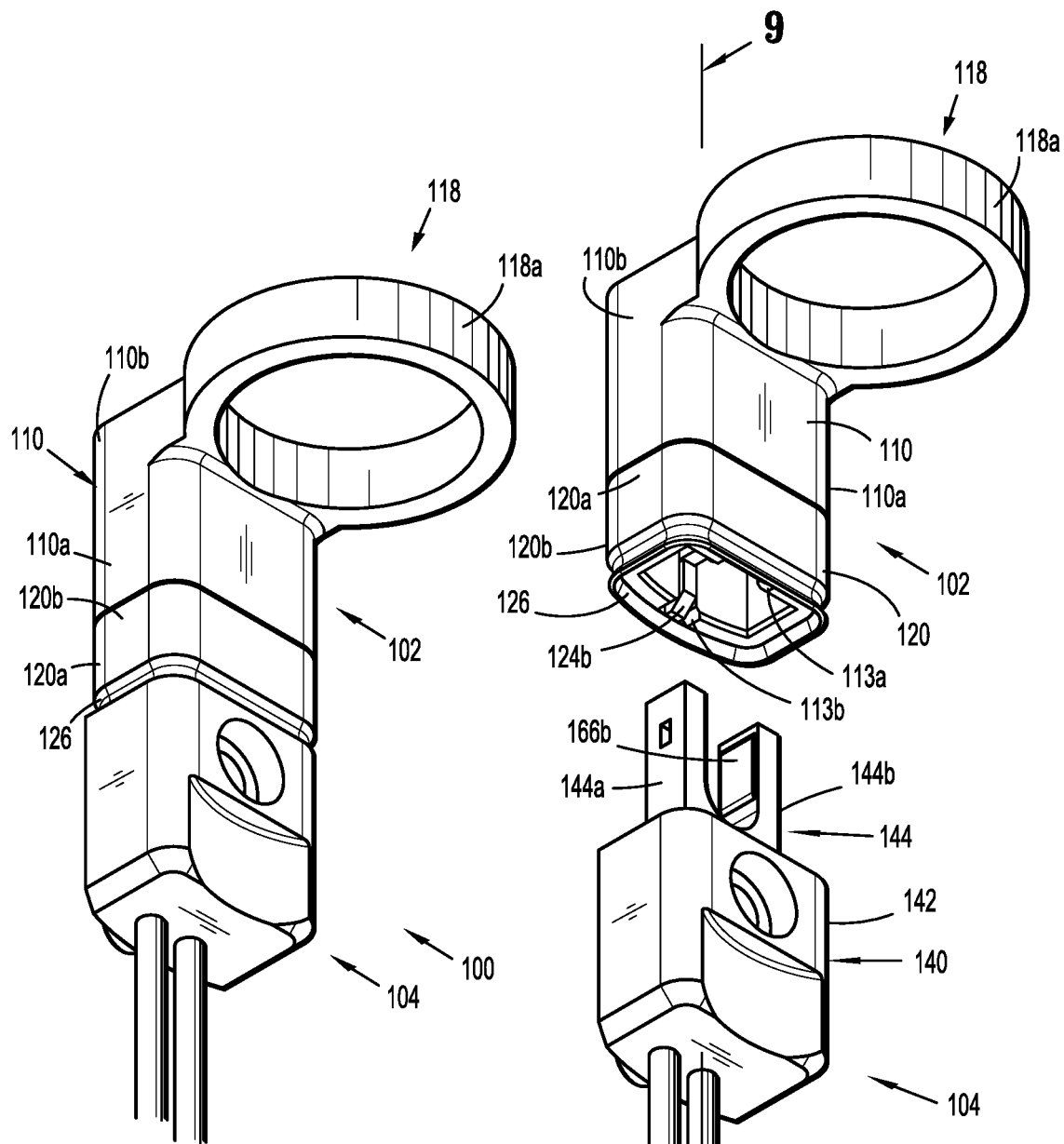
FIG. 5 is a perspective view of a chip assembly according to an embodiment of the present disclosure.
FIG. 6 is a perspective view of the chip assembly shown in FIG. 5 with a housing assembly and a plug assembly separated.

With reference still to FIGS. 7-9, contact members 134a, 134b each include leaf contacts having a substantially flattened C-shape. The contacts are desirably flexible, springy contacts, including the leaf contacts shown. A flange portion 136a, 136b of first and second contact members 134a, 134b is secured to second end 132b of circuit board 132 using adhesive, welding or other method. A contact portion 138a, 138b of each of contact members 134a, 134b extends outwardly from flange portion 136a, 136b, respectively, and includes respective contact surface 135a, 135b. As seen in FIG. 3, contact portions 138a, 138b of contact members 134a, 134b extend outward an amount sufficient to ensure contact between contact portions 138a, 138b of contact members 134a, 134b, respectively, and plug assembly 104.

Turning now to FIGS. 9-11, plug assembly 104 includes a plug member 140, first and second wires 150a, 150b (collectively, wires 150), and a first and second contact members 160a, 160b (collectively, contact members 160). Plug member 140 includes a substantially rectangular base 142 defining a longitudinal axis "x" and a pair of arms 144a, 144b (collectively, arms 144) extending from base 142 parallel to and space from longitudinal axis "x". A shelf 142a extends around arms 144 and is configured to be engaged by flap 126 (FIG. 9) of seal member 120 when arms 144 of plug assembly 104 are operatively received within cavity 111 of housing assembly 102.

As shown, base 142 defines an opening 141 extending perpendicularly through plug member 140 and includes an annular protrusion 143 extending perpendicularly outward from plug member 140. As shown, protrusion 143 is adjacent opening 141. Either or both of opening 141 and protrusion 143 may be used to secure plug assembly 104 to adapter assembly 14 of circular stapler 10 (FIG. 1). First and second arms 144a, 144b are sized and dimensioned to be received within cavity 111 of base member 110 and about circuit board assembly 130 when circuit board assembly 130 is received within slots 111a defined by base member 110.

In one embodiment, plug member 140 is composed of plastic or other moldable material that is formed over contact members 160 after wires 150 are secured to respective first and second contact members 160a, 160b. In this manner, the connection between contact members 160 and wires 150 is sealed from any possible contact with fluids, bodily or otherwise, during a stapling procedure. Alternatively, plug member 140 may include two components that are joined in a fluid tight manner, i.e., welding, adhesive.

With reference still to FIGS. 9-11, a first end of each of first and second contact members 160a, 160b includes a wire connection portion 162a, 162b, respectively, for securing first and second wires 150a, 150b to first and second contact members 160a, 160b, respectively. As shown, wire connection portion 162a, 162b each include a first crimp member 161a, 161b (FIG. 10) configured to be crimped about an exposed portion 152a, 152b of respective, first and second wires 150a, 150b, and a second crimp member 163a, 163b (FIG. 10) configured to be crimped about respective coated portions 154a, 154b of first and second wires 150a, 150b, respectively. Alternatively, wires 150a, 150b may be welded or soldered directly to respective first and second contact members 160a, 160b.

Still referring to FIGS. 9-11, a second end of each of first and second contact members 160a, 160b includes a flange 164a, 164b, respectively and a contact portion 166a, 166b, respectively. Contact portions 166a, 166b of respective first and second contact members 160a, 160b are configured to engage respective contact portions 138a, 138b of contact members 134a, 134b extending outwardly from circuit board 132 of circuit board assembly 130.

As noted above, in one embodiment, plug member 140 is formed by molding base 142 and arms 144 about wires 150 and contact members 160. Specifically, after first and second wires 150a, 150b have been secured to connection portion 162a, 162b of respect first and second contact members 160a, 160b, base 142 of plug member 140 is formed over the first ends of first and second contact members 160a, 160b and first and second arms 144a, 144b are formed about the second ends of first and second contact members 160a, 160b, respectively. First and second arms 144a, 144b are formed about respective first and second contact members 160a, 160b such that respective contact portions 166a, 166b remain exposed. The forming of first and second arms 144a, 144b about flanges 164a, 164b of first and second contact members 160a, 160b creates slots 145a, 145b in respective first and second arms 144a, 144b. Alternatively, first and second arms 144a, 144b are formed with slots 145a, 145b, respectively, to receive flanges 164a, 164b, respectively. First and second arms 144a, 144b each define a throughbore 147a, 147b, respectively, extending perpendicular to longitudinal axis "x". The throughbores assist in the manufacturing process. The throughbores will hold or stabilize the metal contacts during overmolding.

The operation of chip assembly 100 will now be described with reference to FIGS. 2-11. Although adapter assembly 14 and reload assembly 16 are typically provided to a clinician with plug assembly 104 mounted within adapter assembly 14 and housing assembly 102 mounted within reload assembly 16, it is envisioned, that either or both of housing assembly 102 and plug assembly 104 may be secured within respective adapter assembly 14 and reload assembly 16 by a clinician prior to use. Although not shown, it is envisioned that either or both of housing assembly 102 and plug assembly 104 may be spring loaded within respective reload assembly 16 and adapter assembly 14 to allow for positional length tolerances between reload assembly 16 and adapter assembly 14.

As noted above, housing assembly 102 is disposed within reload assembly 16 such that when reload assembly 16 is secured to adapter assembly 14 housing assembly 102 engages plug assembly 104. Specifically, when reload assembly 16 is secured to adapter assembly 14 first and second arms 144a, 144b of plug assembly 104 are received within cavity 111 of housing assembly 102 such that contact portions 166a, 166b of respective first and second contact members 160a, 160b engage respective contact portions 138a, 138b of respective first and second contact members 134a, 134b of circuit board assembly 130. The outward extension of contact portions 138a, 138b of first and second contact members 134a, 134b ensures contact between contact portions 166a, 166b of respective first and second contact members 160a, 160b and contact portions 138a, 138b of respective first and second contact members 134a, 134b. The sweeping motion provided by the spring-like action of contact portions 138a, 138b of respective first and second contact members 134a, 134b further ensures positive contact between first and second contact members 134a, 134b, respectively, of housing assembly 102 and first and second contact members 160a, 160b, respectively. Once housing assembly 102 is connected to plug assembly 104, within adapter assembly 14, it is envisioned that chip 135 will automatically transmit the specifications of reload assembly 16 to handle assembly 12 to ensure handle assembly 12 is configured for use with reload assembly 16. The adapter assembly has wires, which may be disposed in a wire harness inside the adapter assembly, that carry electrical signals from the reload assembly to the controller in the handle assembly.

As discussed above, seal member 120 of housing assembly 102 includes a flap 126 which engages shelf 142a formed on base 142 of plug assembly 104 to create a seal between housing assembly 102 and plug assembly 104. Since contact portions 138a, 138b of respective first and second contact members 134a, 134b and contact portions 166a, 166b of respective first and second contact members 160a, 160b are maintained completely within cavity 111 formed in base member 110 of housing assembly 102, flap 126 of seal member 120 prevents exposure of contact members 134a, 134b, 160a, 160b to any fluids encountered by circular stapler 10 during a stapling procedure. Once circular stapler 10 has been used, reload assembly 16 may be separated from adapter assembly 14 in a traditional manner. A replacement reload assembly 16 may then be secured to adapter assembly 14 for further use of circular stapler 10.

With reference now to FIGS. 12-16, an alternative embodiment of a chip assembly of the present disclosure is shown generally as chip assembly 200. Chip assembly 200 is substantially similar to chip assembly 100 and will only be described in detail as relates to the differences therebetween. Chip assembly 200 includes a configuration substantially similar to a headphone-style" plug and jack. In particular, chip assembly 200 includes a housing assembly 202 and a plug assembly 204 configured to selectively engaged housing assembly 202. Housing assembly 202 is configured to be securely mounted within reload assembly 16 (FIG. 1) and is configured to be securely mounted within a distal end 14b of adapter assembly 14 (FIG. 1) such that when reload assembly 16 is secured to adapter assembly 14 housing assembly 202 engages plug assembly 204.

Figure 14:
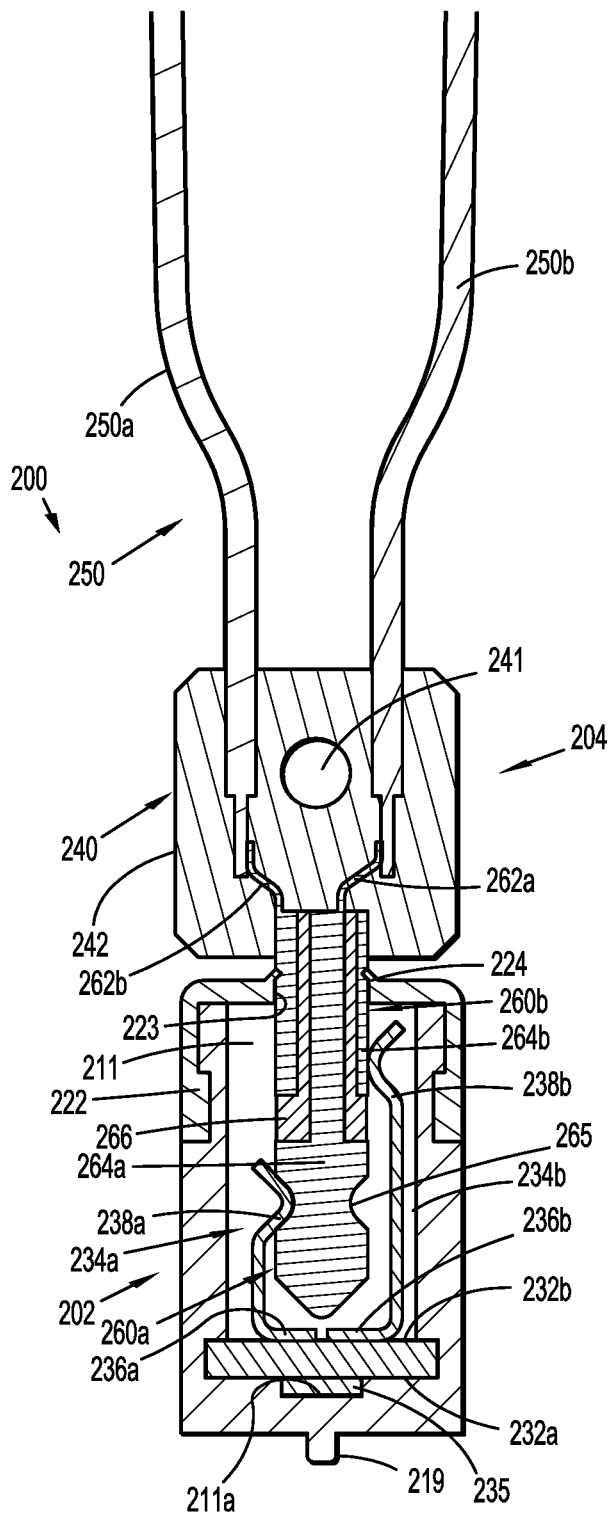
FIG. 14 is a cross-sectional side view of the chip assembly shown in FIG. 12.
Figure 15:
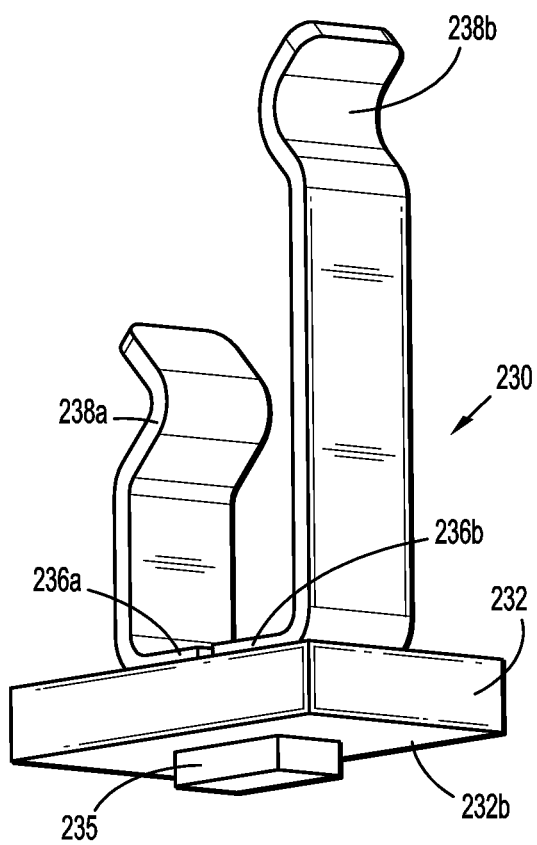
FIG. 15 is a perspective view of a circuit board assembly of the housing assembly shown in FIG. 14.
Figure 16:
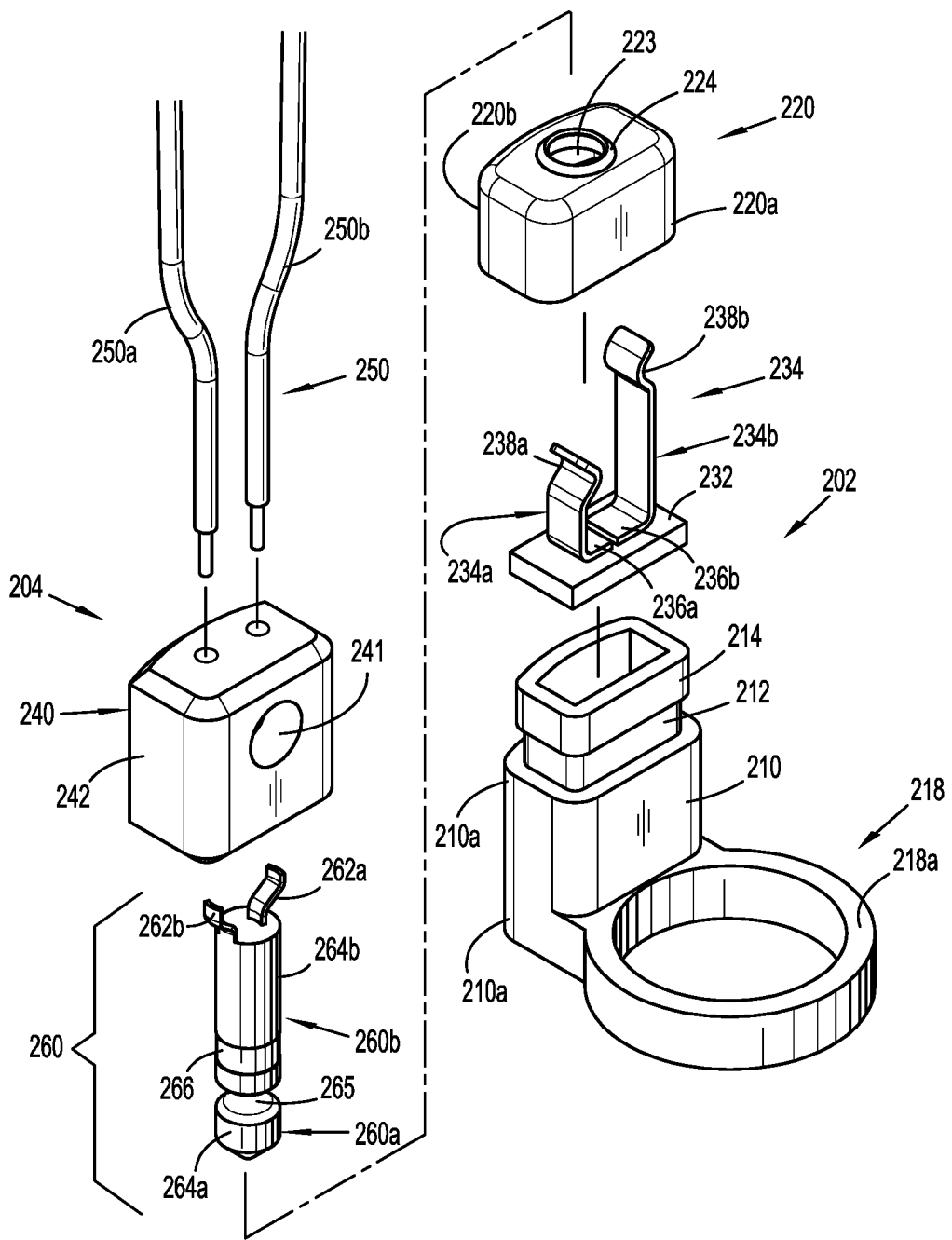
FIG. 16 is an exploded perspective view of the chip assembly shown in FIG. 12.

With particular reference to FIGS. 14 and 16, housing assembly 202 includes a base member or housing 210, a seal member 220, and a circuit board assembly 230 (FIG. 15). Base member 210 defines a cavity 211 and includes an open first end 210a and a closed second end 210b. Base member 210 may be formed monolithically by molding base member 210 over circuit board assembly 230. In this manner, cavity 211 forms a fluid tight cavity. Alternatively, base member 210 may be formed in two components that are sealed together in a fluid tight manner, i.e., by welding, with adhesive.

With reference still to FIGS. 14 and 16, first end 210a forms an extension 212 configured to engage seal member 220. Specifically, extension 212 is formed by a recessed portion of base member 210 having a flange 214 extending about an end of extension 212 configured to engage a lip 222 on seal member 220. The reduced outer dimensions of extension 212 allows seal member 220 to lay flush with base member 210. Base member 210 also defines a slot 211a in communication with cavity 211 sized to receive chip 235 of circuit board assembly 230.

Base member 210 further includes a connection member 218 for securing housing assembly 202 within reload assembly 16 (FIG. 2). As shown, connection member 218 includes an annular flange extending perpendicular to a longitudinal axis "x" of base member 210. Annular flange 218a is configured to be received about a tubular portion of reload assembly 16. Although shown as an annular flange, it is envisioned that connection member 218 may include a C-shaped flanged (not shown) for selective attachment to reload assembly 16. Alternatively, fastener member 218 may include one or more tabs and/or slots configured to secure base member 210 within reload assembly 16. Base member 210 further includes one or more alignment features 219. As shown, alignment feature 219 forms a protrusion extending outwardly from closed second end 210b of base member 210. Alignment feature 219 facilitates alignment of base member 210 within reload assembly 16.

Seal member 220 includes a substantially annular body having an open first end 220a and a substantially closed second end 220b. First end 220a includes lip 222 extending about an inner surface of seal member 220. As discussed above, lip 222 is configured to engage flange 214 formed on extension 212 of base member 210. Second end 220b of seal member 220 defines a circular opening 223 and includes an annular flange formed 224 formed about opening 223. Flange 224 is configured to form a seal between housing assembly 202 and plug extension 260 of plug assembly 204 when plug assembly 204 engages housing assembly 202.

With reference now to FIGS. 14 and 15, circuit board assembly 230 includes a circuit board 232, first and second contact members 234a, 234b (collectively, contact members 234) and a chip 235. Circuit board 232 defines a substantially planar elongate member configured to be securely received within slot 211a defined by base member 210. A first surface 232a of circuit board 232 supports chip 235 and a second surface 232b of circuit board 232 supports first and second contact members 234a, 234b. The contact members may be flexible, springy members, similar to those discussed above. Chip 235 is in electrical communication with contact members 234. As discussed above, Chip 235 includes any commercially available chip capable of storing (permanently or temporarily) the specifications of reload assembly 16 (FIG. 1), i.e., cartridge size, staple arrangement, staple length, clamp-up distance, and transmitting the specifications to handle assembly 12. It is further envisioned that chip 235 may include write capabilities which allow handle assembly 12 to encode that a reload assembly has been used, to chip 235 to prevent reuse of an empty reload assembly, or for any other purpose. In one embodiment, chip 235 includes an erasable programmable read only memory ("EPROM") chip.

Contact members 234a, 234b each include a flange portion 236a, 236b, respectively, for mounting contact member 234a, 234b, respectively, to circuit board 232 and a crimped portion 238a, 238b for contacting first and second contact portions 264a, 264b of plug assembly 204. Flange portions 236a, 236b are secured to circuit board 232 using adhesive, welding or other suitable method. Flange portions 236a, 236b are secured to circuit board 232 such that crimped portions 238a, 238b extend parallel to one another and are configured to engage plug member 240 of plug assembly 204 therebetween. Crimped portion 238b of contact member 234b is longer then crimped portion 238a of contact member 234a. As such, crimped portion 238b extends a greater distance into cavity 211 from circuit board 232 than crimped portion 238a of contact member 234a. As will be discussed in greater detail below, the increased length of crimped portion 238b of contact member 234b allows crimped portion 238b to engage a different portion of plug member 240.

The crimped portion can be bent, crimped, or recessed or otherwise shaped to facilitate the connection described herein.

Figure 13:
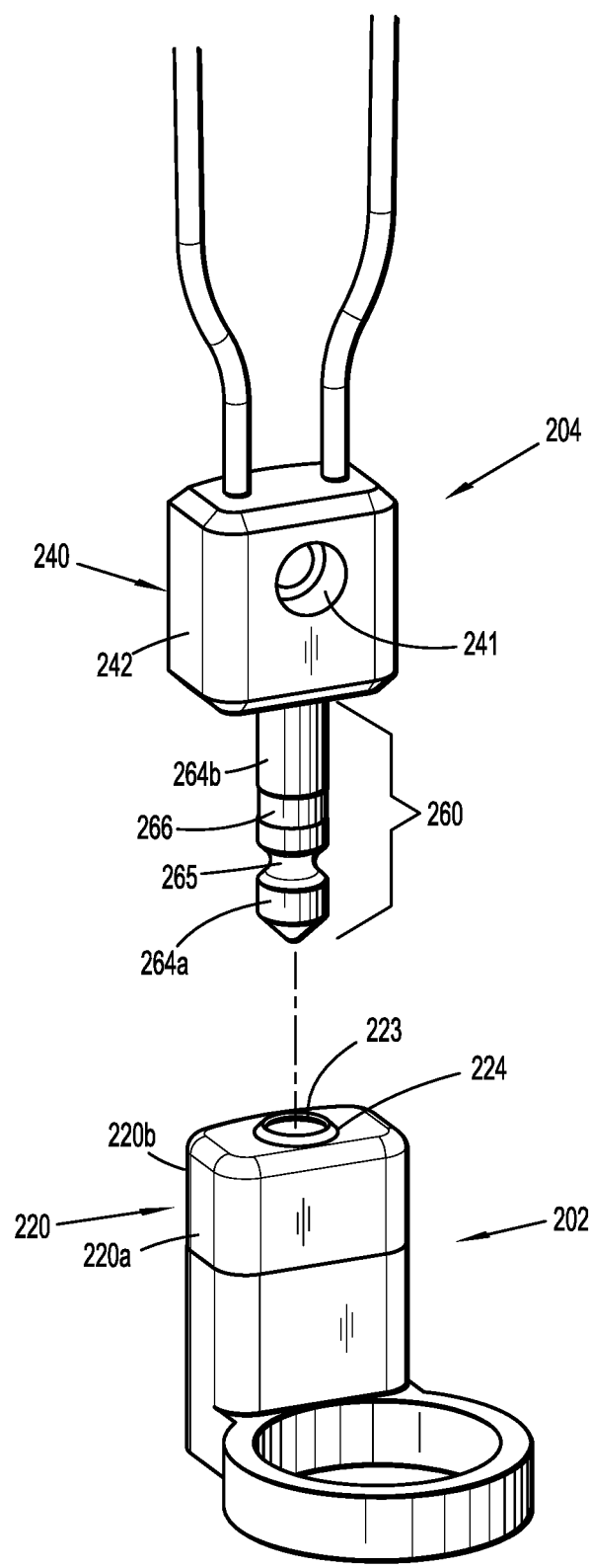
FIG. 13 is a perspective view of the chip assembly shown in FIG. 12 with the housing assembly and plug assembly separated.

Turning now to FIGS. 13, 14, and 16, plug assembly 204 includes a plug base 240, first and second wires 250a, 250b (collectively, wires 250), and a plug extension 260 including first and second contact members 260a, 260b. Plug base 240 includes a substantially rectangular member defining a longitudinal axis "x". As shown, plug base 240 defines an opening 241 extending perpendicularly through plug base 240. Opening 241 may be used to secure plug assembly 204 within adapter assembly 14 of circular stapler 10. Plug base 240 is composed of plastic or other moldable material that is formed over connector portions 262a, 262b of first and second contact members 260a, 260b, respective, after respective wires 250a, 250b are secured to respective first and second contact members 260a, 260b.

Still referring to FIGS. 13, 14, and 16, a first end of each of first and second contact members 260a, 260b includes wire connection portions 262a, 262b, respectively, for securing first and second wires 250a, 250b to first and second contact members 260a, 260b, respectively. As shown, each wire 250a, 250b is connected to respective wire connection portion 262a, 262 by welding, soldering, or other suitable method. Alternatively, wire connections portions 262a, 262b of first and second contact members 260a, 260b, respectively, may include fasteners for securing wires 250a, 250b to first and second contact members 260a, 260b, respectively.

A second end of each of first and second contact members 260a, 260b includes a contact portion 264a, 264b, respectively. Contact portion 264a of first contact member 260a is in the form of a solid cylindrical body defining a groove 265a. As seen in FIG. 14, groove 265 is positioned to receive crimped portion 238a of first contact member 234a of housing assembly 202 when plug extension 260 is received within cavity 211. Contact portion 264b of second contact member 260b is in the form of an annular body. Contact portion 264b is configured to engage crimped portion 238b of second contact member 234b. Contact portions 264a, 264b are separated by an insulation member 266 As noted above, plug base 240 is formed about wires 250 and connection portions 262a, 262b of first and second contact members 260a, 260b. Thus, the contact portions of the plug assembly are formed on the plug extension 260 as contact portions separated from one another by the insulation member of the plug extension.

Specifically, after wires 250a, 250b are secured to connection portion 262a, 262b of respect first and second contact members 260a, 260b, plug base 240 is formed over connection portions 262a, 262b of first and second contact members 260a, 260b. Other methods of manufacture are also contemplated.

Chip assembly 200 operates in a substantially similar manner to chip assembly 100. In particular, as noted above, housing assembly 202 is disposed within reload assembly 16 (FIG. 1) such that when reload assembly 16 is secured to adapter assembly 14 (FIG. 1) plug assembly 204 engages housing assembly 202. Specifically, when reload assembly 16 is secured to adapter assembly 14 plug extension 260 of plug assembly 204 is received within cavity 211 of housing assembly 202 such that contact portions 264a, 264b of respective first and second contact members 260a, 260b engage respective crimped portions 238a, 238b of respective first and second contact members 234a, 234b of circuit board assembly 230. The increased length of crimped portion 238b of second contact member 234b ensures second contact member 234b engages contact portion 264b of second contact member 260b. The sweeping motion provided by the engagement of crimped portions 238a, 238b of respective first and second contact members 234a, 234b with contact portions 264a, 264b of respective first and second contact members 260a, 260b further ensures positive engagement between first and second contact members 234a, 234b, respectively, of housing assembly 202 and first and second contact members 260a, 260b, respectively.

As discussed above, seal member 220 of housing assembly 202 includes a flap 226 which engages plug extension 260 of plug assembly 104 to effective seal cavity 211 of housing assembly 202. Since crimped portions 238a, 238b of respective first and second contact members 234a, 234b and contact portions 264a, 264b of respective first and second contact members 260a, 260b are maintained completely within cavity 211 formed in base member 210 of housing assembly 202, flap 226 of seal member 220 prevents exposure of contact members 234a, 234b, 260a, 260b to body fluids during use of circular stapler 10 (FIG. 1). In this manner, chip assembly 200 is sealed from contact with any body fluids which adapter assembly 14 and reload assembly 16 may encounter during a stapling procedure using circular stapler 10.

It is contemplated that a system of components can use chip assemblies incorporated in reload assemblies, adapter assemblies, and/or handle assemblies to provide a variously configurable surgical instrument that prevents reuse of previously used components, prevents use of unauthorized components, promotes the proper use of components, and stores and provides data concerning the use of the surgical instrument. Such system can include surgical staplers, clip appliers, electrosurgical devices, diagnostic devices, etc.

In any of the embodiments disclosed herein, the handle assembly can have a controller, drive mechanism, and power source. The controller includes a memory unit and processor for reading the data from the chip, and/or controlling the operation of the instrument, and/or storing data. The controller can include ROM, RAM, magnetic memory devices, optical memory devices, MEMS, magneto-optical or electronic memory, PC card PCMCIA devices, etc. The handle assembly can also include buttons, display screens and other interfaces for the user's convenience. The handle assembly may be configured and arranged as disclosed in U.S. Published Application 2013/0098968, WO 2009/039506, U.S. Published Application 2011/0121049, the disclosures of each of which are hereby incorporated by reference herein in their entirety.

The drive mechanism can include a set of gears and one or more motors, providing an electromechanical surgical system. The power source can be a battery, line current, a DC power supply, an electronically controlled DC power supply, etc. It is also contemplated that the surgical system can be a robotic surgical system having removable and replaceable reload assemblies, with the chip assembly described above.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A chip assembly for use in a surgical stapler, the chip assembly comprising:

a housing assembly configured to be mounted within a reload assembly, the housing assembly including a base member, a circuit board assembly disposed within the base member, and a seal member received about an end portion of the base member; and a plug assembly configured to selectively engage the end portion of the base member, the plug assembly including a plug member, a plug extension extending from the plug member and receivable through the seal member, the plug extension including a first contact member, a second contact member disposed about the first contact member and an insulation member disposed between the first and second contact members, wherein the first and second contact members are configured to engage the circuit board assembly when the plug assembly engages the housing assembly.

2. The chip assembly of claim 1, wherein the housing assembly is configured to be mounted within a reload assembly of the surgical stapler.

3. The chip assembly of claim 1, wherein the plug assembly is configured to be mounted within an adapter assembly, the adapter assembly being configured to interconnect a reload assembly and a handle assembly.

4. The chip assembly of claim 1, wherein the seal member forms a fluid tight seal with the base member and the plug member.

5. The chip assembly of claim 1, wherein a contact portion of the first contact member is longitudinally spaced from a contact portion of the second contact member.

6. The chip assembly of claim 1, wherein the housing includes a connection member for securing the housing assembly within a reload assembly.

7. The chip assembly of claim 6, wherein the connection member includes an annular flange.

8. The chip assembly of claim 1, wherein the circuit board assembly includes a chip.

9. The chip assembly of claim 8, wherein the chip is an EPROM chip.

10. The chip assembly of claim 8, wherein the chip is configured to contain specifications of the reload assembly in which the housing assembly is mounted.

11. The chip assembly of claim 8, wherein the chip is writeable.

12. The chip assembly of claim 1, wherein the circuit board assembly includes a pair of contact members.

13. The chip assembly of claim 12, wherein the first and second contact members of the plug member are configured to engage the pair of contact members of the circuit board assembly when the plug assembly engages the housing assembly.

14. The chip assembly of claim 1, wherein the plug member is monolithically formed.

15. The chip assembly of claim 1, wherein the plug member is overmolded about the first and second contact members.

16. A chip assembly for use in a surgical stapler, the chip assembly comprising:

a housing assembly configured to be mounted within a reload assembly, the housing assembly including a base member, a circuit board assembly disposed within the base member, and a seal member received about an end portion of the base member, the circuit board assembly including first and second contacts members, each of the first and second contact member of the circuit board assembly includes a crimped portion, the crimped portion of the first contact member of the circuit board assembly is longitudinally spaced from the crimped portion of the second contact member of the circuit board assembly; and a plug assembly configured to selectively engage the end portion of the base member, the plug assembly including a plug member and a plug extension extending from the plug member and receivable through the seal member, the plug extension including a first contact member and a second contact member disposed about the first contact member, wherein the first and second contact members of the plug extension are configured to engage the respective first and second contact members of the circuit board assembly when the plug assembly engages the housing assembly.

17. The chip assembly of claim 16, wherein the first contact member of the housing assembly defines a groove, the crimped portion of the first contact member of the circuit board assembly being releasably receivable with the groove when the plug assembly engages the housing assembly.

* * * * *